United States Patent [19]
Weinrib

[11] Patent Number: 4,785,809
[45] Date of Patent: Nov. 22, 1988

[54] ARTERIOTOMICAL DEVICE

[76] Inventor: Harry P. Weinrib, 2644 West Estes Ave., Chicago, Ill. 60645

[21] Appl. No.: 855,136

[22] Filed: Apr. 23, 1986

[51] Int. Cl.⁴ .............................................. A61B 17/32
[52] U.S. Cl. ..................................................... 128/305
[58] Field of Search ............... 128/751, 305, 318, 325, 128/346, 326

[56] References Cited
U.S. PATENT DOCUMENTS

| | | | |
|---|---|---|---|
| 2,076,468 | 4/1937 | Breck | 128/305 |
| 3,837,345 | 9/1974 | Matar | 128/305 |
| 4,018,228 | 4/1977 | Goosen | 128/305 |
| 4,162,678 | 7/1979 | Fedotov et al. | 128/305 |
| 4,597,385 | 7/1986 | Watson | 128/751 |

Primary Examiner—Michael H. Thaler
Attorney, Agent, or Firm—Fitch, Even, Tabin & Flannery

[57] ABSTRACT

A surgical instrument cuts openings in tissue with a more precise and consistent size. The instrument includes a lifter having a hook for hooking a portion of the tissue and for lifting the hooked tissue relative to a gauge. Pivotally mounted cutters on the instrument are swung towards the lifted tissue to sever the lifted tissue leaving an opening of a known size in the tissue.

13 Claims, 2 Drawing Sheets

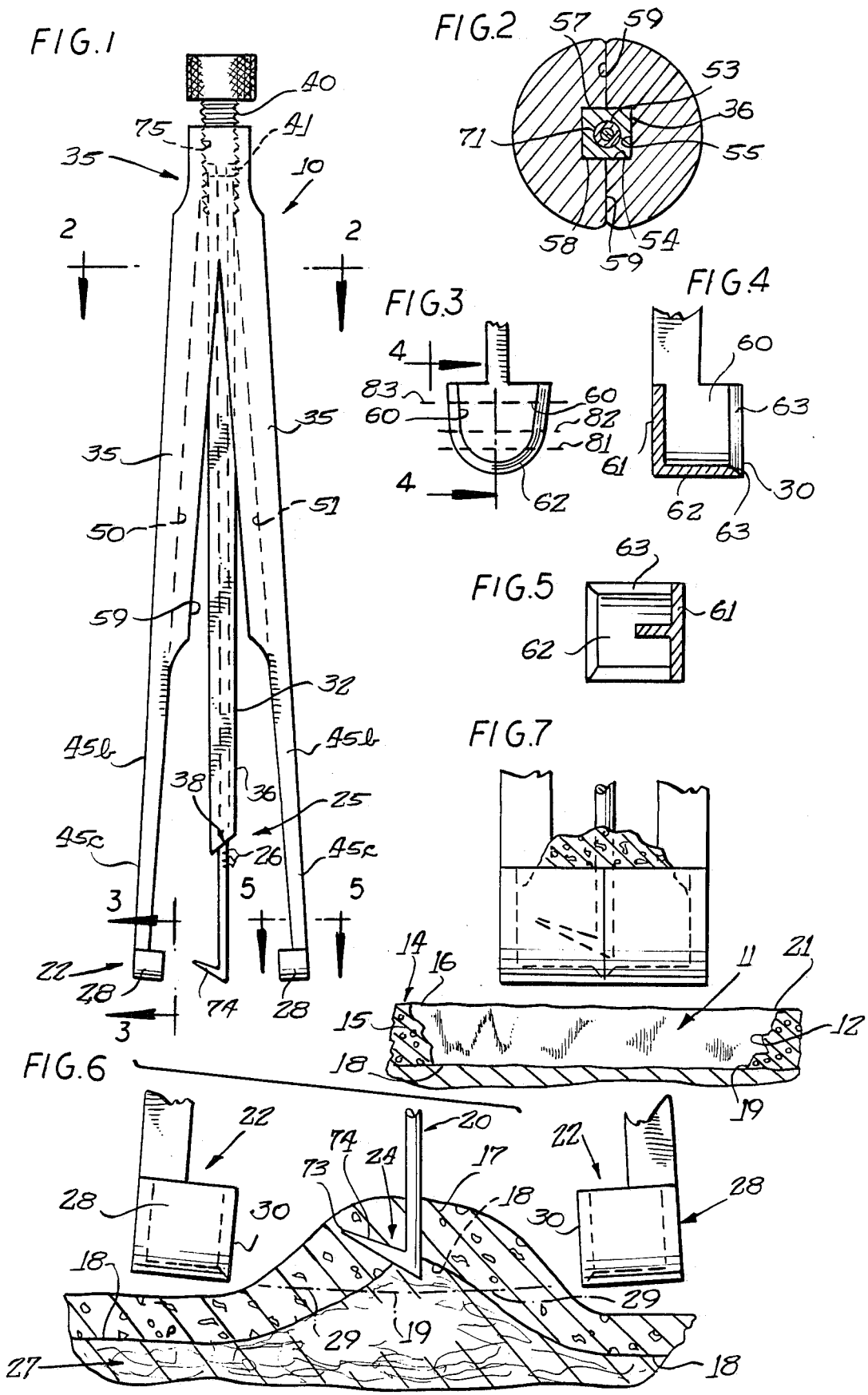

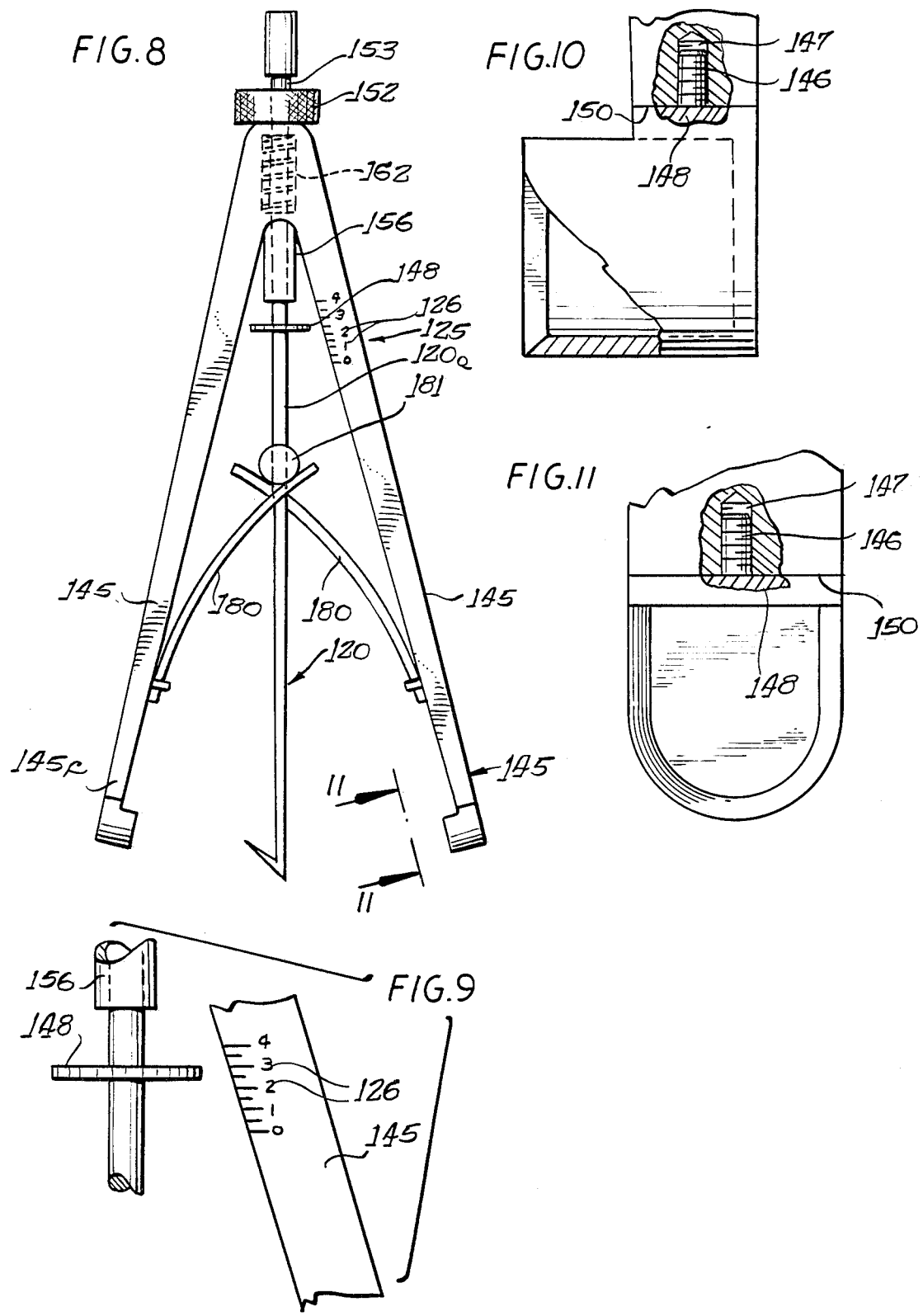

ARTERIOTOMICAL DEVICE

BACKGROUND OF THE INVENTION

This invention relates to a surgical instrument to be used by a surgeon to sever living tissue and, more particularly, to cut openings of a predetermined size in the tissue such as vessels or the like.

The present invention is directed to cutting of living tissue to form openings therein of a predetermined size and is particularly useful for cutting openings in tubular anatomical vessels, such as blood vessels, ureter, vas deferens, fallopian tubes and biological sheaths for nerve bundles and will be described hereinafter in connection with the preferred use which is as in arteriotomical instrument for cutting holes into blood vesesls to which will be attached another donor vessel by an anastomosis technique. Typically, in an arteriotomical procedure, the surgeon will locate the area which the anastomosis is to be made and with a first instrument, such as a forceps, or a curved surgical needle lift, and pull a portion of the recipient vessel outwardly and then use his other hand with a scalpel or a scissors to cut about the lifted portion to form the opening in the vessel. The size of the opening should match the outer diameter of the donor vessel and the opening size is estimated by the surgeon based on his experience. In many instances, as in microsurgery, the donor vessel may be very small, e.g. about one, two or three millimeters in diameter. For best results, the size of the opening should be such that the new donor vessel be stretched slightly and certainly not compressed in size, when secured to the recipient vessel, to prevent a reduction in size of donor vessel lumen. Thrombosis at the anastomosis site may occur if the vessel lumen is constricted and blood flow is obstructed thereby. If the cut opening is made too large, then it is difficult to connect the new vessel to the first vessel without leakage at the sutured connection between the vessels.

Additionally, it is often difficult for the surgeon because of the space limitation of the surrounding tissue and other living material to be able to manipulate the scalpel or scissors to obtain a good, uniform, circular cut to form the opening in the vessel. Often the surgeon is located on one side of the vessel, used called the control side, and has difficulty in making a true semi-circular cut on the opposite obscured or non-control side. Also, the opening being cut by the surgeon in conventional techniques is adversely affected by having a thicker vessel wall than anticipated because of the accumulation of arteriosclerotic material on the intima of the vessel. More specifically, the surgeon gauges his cut on the exterior of the blood vessel and his incision is at an inclined angle such that the thicker the wall the smaller will be the opening into the lumen. Thus, where the vessel wall has substantial increase in wall thickness due to arteriosclerotic material accumulation, the interior opening will be smaller than anticipated. With the present invention, however, the thickness of the wall does not adversely affect the size of the hole at the interior of the vessel because the cut is sized from the interior of the vessel wall. Also, with the present invention, the cut is made automatically and is made generally circular and gauge means are provided on the instrument. Thus, the surgeon is provided with an indication of the size of opening that will be cut with the instrument so that the surgeon may match more accurately the opening size to the donor vessel size and the surgeon may obtain uniform and consistent sizes of openings.

Further, the instrument is easy to use and may save surgical time which is very important in situations where the anastomosis is desired to be done as quickly as possible to allow resumption of blood flow as soon as possible.

Accordingly, a general object of the invention is to provide a new and improved surgical instrument for cutting openings in living tissue.

A more specific object of the invention is to provide a new and improved arteriotomical instrument for cutting openings in blood vessels.

These and other objects and advantages of the invention will become apparent from the following detailed description and accompanied drawings in which

DETAILED DESCRIPTION OF THE DRAWINGS

FIG. 1 is a view of a surgical instrument embodying the novel features of the invention.

FIG. 2 is a cross sectional view which has been enlarged and which has been taken substantially along the line 2—2 of FIG. 1.

FIG. 3 is an enlarged view of a cutting end instrument taken in a direction illustrated by the line 3—3 of FIG. 1.

FIG. 4 is a cross sectional view taken substantially along the line 4—4 of FIG. 3.

FIG. 5 is an enlarged cross sectional view taken substantially along the line 5—5 of FIG. 1.

FIG. 6 is an enlarged fragmentary view of the cutters about to cut a lifted piece of vessel wall.

FIG. 7 illustrates the cutters having severed the lifted piece, leaving a hole in the vessel wall.

FIG. 8 is a surgical instrument constructed in accordance with another embodiment of the invention.

FIG. 9 is an enlarged fragmentary view of a gauge means used on the instrument of FIG. 8.

FIG. 10 is an enlarged, side elevational, partially broken away view of a cutter.

FIG. 11 is an end view of a cutter looking in the direction of the arrows 11—11 in FIG. 8.

As shown in the drawings for purposes of illustration, the surgical instrument 10 is shown for use in severing an opening or hole 11, as best seen in FIG. 7 defined by an encircling wall 12 formed in a piece of living tissue 14 which is herein as illustrated in the form of a blood vessel 15, although the living tissue may be any type of tubular anatomical structure or vessel. The end use of the present invention is not limited to any particular surgical technique or to any particular kind of living tissue. Conventionally, a surgeon will use a forceps or a surgical needle to lift a portion 17 of the vessel, as shown in FIG. 6, and then with a scalpel or scissors (neither of which is shown), the surgeon will then make a generally circular cut to remove the lifted tissue leaving behind the opening 11 to which will be attached another donor vessel usually by anastomosis techniques to assure continued patency.

It will be appreciated that the surgeon must generally estimate the size of the opening from his view of an exterior wall or surface 16 of the vessel and he will cut without any tools, aids or gauges. He usually knows the diameter of the donor vessel and he estimates by past experience how much to lift the recipient vessel and where to make his encircling cut. The size of the hole may vary depending upon the amount of lifted material, that is the height, or the material is pulled outwardly from the vessel, the thickness of the vessel wall between the exterior surface 16 and an interior surface 18, and the radius of the path his scalpel or scissors takes about the lifted point which will be generally the center of the opening 11 cut in the vessel 15. The accumulation of arteriorsclerotic material makes the vessel wall thicker between its exterior and interior surfaces and the inclined or oblique nature of the cut will make an interior aperture 19 in the interior wall 18 substantially smaller than an outer aperture 21 for the hole 11 in the exterior wall 16. Because the donor vessel diameters are very small, a mistake in estimation by the surgeon can easily result in an opening which varies by significant percentage from the donor vessel diameter.

In accordance with the present invention, a more precisely sized and a more consistent size of opening 11 may be cut in the tissue 14 such as a vessel 15 by the surgical instrument 10 which includes a lifter 20 for lifting the vessel portion 17 which is then severed from the vessel 15 by means of movable cutter means 22 on the instrument. More specifically, the cut is achieved in the present invention by hooking a hook means in the form of a barb or hook 24 on the lifter into the vessel portion 17 and moving the lifter 20 upwardly and relative to a gauge means 25 which is marked with indicia 26 to show the amount of lifting of the vessel portion 17 relative to the cutter means 22. The cutter means 22 on the instrument 10 are preferably pivotally mounted for swinging movement toward one another to bring pivotal cutters 28 toward one another with the cutting blades or edges 30 moving along the cut lines 29, shown in FIG. 6, to sever the portion 17 which is then removed as shown in FIG. 7 leaving the opening 11 as defined by the wall 12.

The hook 24, as best seen in FIG. 6, is pushed through the wall of the blood vessel 15 into a lumen 27 and then lifted to cause the hook to pierce the interior surface 18 of the vessel. When there is arteriosclerotic material making the wall thicker, the hook 24 pierces the arteriosclerotic material and is limited thereby. Because the cutting edges 30 are related to the position of the hook, the interior aperture 19, which is shown in dotted lines in FIG. 6, is made to the given size because the control for the size of the hole 11 is from the interior of the vessel rather than from the exterior of the vessel as in conventional practice.

Thus, it will be seen that the method of the present invention involves the steps of: hooking of the interior wall 18 of a vessel 15, lifting a portion 17 of the vessel, and moving cutters 28 along a predetermined path related to the hook 24 and lifted portion 17 so that the interior aperture 19 for the hole 11 is of a known size. In this method, the lifter 20 is raised relative to the gauge means 25 which is gauged as to the size of the hole 11, e.g., one, two or three millimeters in microsurgery.

In this preferred embodiment of the invention, the lifter 20 carries an at its upper end in a frame portion 35 to which are also pivotally mounted the movable cutters 28. The illustrated and preferred lifter 20 carries an indicator 38 in the form of indicia 26 on the lifter 28 which moves vertically relative to a pointer 38 on a stationary tube 32 as the lifter is moved vertically to indicate the position of the hook 24 relative to the movable cutters 28. The lifter may be actuated for movement in various manners. To this end, the illustrated lifter 20 has an upper threaded end 40 threaded in a nut portion 41 in the frame so that by turning the threaded screw 40, the hook 24 is moved vertically. As the lifter 20 moves vertically, the indicia 26 moves past the arrow indicator 38 showing where the hook 24 is in relationship to the cutters 28 and the interior wall 18 of the vessel so that the surgeon may make a consistent size hole 11 whenever he has lifted the same kind of vessel to the same point on the gauge means for the desired size opening. Thus, it is possible with experience to continually return a given indicia 26 to the indicator 38 and obtain the same size of hole 11 when swinging the movable cutters 28 to sever the portion 17.

The preferred instrument may be made very small and used in microsurgery; and, in such event, the cutters 28 need to be precisely aligned at the ends of the long legs 45 which carry the cutters. To this end, it is preferred that there by an alignment means which continually operating to assure alignment of the cutting edges 30 through out their travel between two fully opened position of FIG. 1 and fully closed position of FIG. 7. The preferred alignment means includes a square cross section vertical bar 36 through which slides the lifter 20, as best seen in FIG. 2. The bar 36 is fixed to the frame 35 at its upper end and fits within complementary size vertical slots 50 and 51 formed in inwardly facing sides of the respective legs 45. The slots are formed with vertical side walls 53 and 54 and an intersecting back wall 55 which will abut the square cross section 20 when the legs are brought together to the closed position such as shown in FIG. 7. Sides 57 and 58 of the lifter bar 36 having sliding engagement with the sidewalls 53 and 54 of the slot to hold the legs in alignment.

Referring now in greater detail to the illustrated embodiment of the invention, the preferred shape for the legs 45 is that the upper portions 45a thereof are generally semi-cylindrical in shape on the outer surfaces thereof such that when flat inner vertical faces 59 on the legs are brought together the outer surfaces 35 combine to form a pencil like cylinder which can be rotated easily by the surgeon, particularly by a surgeon who is specializing in microsurgery. The upper ends of the legs 45 are welded or otherwise joined or integrally formed with the central frame 35. The two legs 45 are formed to be naturally expand to the open position shown in FIG. 1 much in the manner of the typical forceps and the legs are pressed together against the spring force in the legs to do the cutting. The lower ends 45b of the legs are tapered and thinner in cross section than the upper ends and at their lower ends or tips 45c are the cutters 28.

The preferred shape for the cutters 28 is generally box-shaped, and as shown in FIG. 3, the cutting edges 30 have a U-shape. More specifically, the box-shaped cutters have a pair of side walls 60, an outer back wall 61, and an arcuate bottom wall 62. The side walls 60 and the bottom wall 62 each have cutting edges 30, as shown in FIG. 4. The side walls 60 have the vertical cutting edges 30 as shown in FIGS. 3 and 4. Herein, the cutting edges 30 are each formed by a slanted or tapered edge wall 63 ending in the sharp cutting edge 30.

As best seen in FIG. 6, the box-shaped cutters have their respective U-shaped cutting edges 30 facing one another and when the surgeon presses the legs 45 toward each other the U-shaped cutting edges 30 will move inwardly along the lines 29 shown in FIG. 6 to cut the tissue 17 which has been lifted by the hook 24 and lifter 20 into the lifted position shown in FIG. 6.

The cutters are brought together, as shown in FIG. 7, with the cutting edges 30 abutted on the respective cutter means, and with the severed lifted portion 17 disposed within the box-shaped portion formed by the cutters. After cutting the vessel wall along the line 29, the walls 12 forming the hole 11 will snap downwardly from the position of FIG. 6 to the position of FIG. 7 leaving an upper aperture in the exterior surface 16 of the vessel leading to the slightly inclined side wall 12 and terminating in the aperture 19 in the lower interior surface 18 of the vessel. Opening 11 will be slightly oval in shape rather than a true circle, and the hole wall 12 will be slightly inclined rather than straight vertical. However, the diameter of the opening 11 and the diameter of the donor vessel (not shown) can be matched by use of the instrument 10 such that the aperture 19 in the interior wall is correctly sized to the end of the donor vessel, which is to be secured to the vessel 15 and generally extended at right angles thereto. Suitable suture and anastomosis techniques are used to connect the right angle vessel to the illustrated vessel 15.

The preferred lifter 20 is a steel wire which may be a piece of steel catheter wire mounted in a surrounding stationary hollow tube 71 (FIG. 2) which is mounted in the fixed alignment bar 36. The hollow tube 71 is the usual protective catheter tube of small diameter having a hollow vertical bore in which slides the catheter wire lifter 20. The catheter hollow tube 71 is fixed in a hollow vertical bore of the bar 36. The lifter 20 is thus guided for sliding vertical movement within the hollow vertical tube and is prevented from bending or kinking by the tube 71. The lower end of the wire lifter is flattened and then shaped to form the hook 24 which has a sharp point 73 on the end of an upwardly and outwardly inclined barb. Manifestly, the hook may have more than one barb and may have various shapes. The catheter wire lifter is very smaller in diameter as its surrounding tube and the bar 36. A surgical needle may be formed with a hook and used in lieu of a catheter wire, if so desired. Manifestly, other forms of lifters may be used in lieu of the preferred and illustrated lifter.

The upper end of the wire lifter 20 is secured as by swivel 75 on the lower end of the threaded screw 40. Turning of the screw 40 in the threaded nut 41 of the frame 35 pulls the swivel 75 and the upper end of the wire lifter 20 vertically without rotating the hook 24. That is, the swivel 75 serves as a connection which allows the screw to rotate and lift the lifter 20 without rotating the lifter. As the lifter raises, each of the indicia 26 is serially moved within the bar 36 and past the indicator 38 on the bar 36. Herein, the indicia are marked "1", "2", and "3" to indicate the aperture size 19 in the interior wall 18 will be a corresponding one, two or three millimeter in diameter. On the cutter 28 in FIG. 3, are marked three lines 81, 82, and 83 each of which symbolizes where the hook 24 will be raised relative to the bottom end 84 of the cutter 28. For example, if the hook 24 raises the lifted portion's interior surface 18 to the line 81, then a one millimeter diameter aperture 19 will be cut in the interior wall 18. If the hook is raised to lift the interior surface 18 to the line 82, then a two millimeter diameter aperture 19 will be formed in the interior surface 18. Likewise, raising the lifted portion higher to the line 83, will result in a three millimeter hole 11. The lines 81, 82, and 83 are not to scale and are for illustration purposes only. For large size holes 11, the cutters 28 may be replaced with large cutters, as will be explained in connection with FIG. 8.

In accordance with the further embodiment of the invention, which is shown in FIG. 8, the elements similar to those previously described will now be described with the prefix "1" before each element previously described. The instrument 110 includes a lifter 120 having a hook 124. Legs 145 for the instrument 110 carry a pair of arcuate leaf springs 180 each of which abuts a common member 181 through which passes the lifter shaft 120a. The springs 180 hold the movable legs 145 apart. On the lifter 120 is mounted indicator or arrow 148 for cooperating with indicia 126 on a gauge means 125.

Herein, each of the cutter or cutter means 128 is detachably mounted to lower ends 145c of the legs 145 as by threaded screw studs 146 secured to the top wall 148 and threaded into a threaded opening 147 formed in a bottom wall 150 on the tips 145c of each leg. Thus, if the instrument should be dropped or the blade should be so dull as to desire to use a sharper blade or to use blades of different cutting configuration from the U-shape herein, the cutters 28 may be unthreaded and removed and replaced by new cutters which may be then threaded into the threaded openings and held therein until the top wall 148 on the cutter is tightly abutted against the flat surface 150 on the bottom of the leg tips 145c.

In the surgical instrument 110, the lifter 120 is moved vertically by turning an adjustable nut 152 mounted on a threaded end 153 of the lifter 120 so that the turning thereof moves the lifter 120 vertically within the portion 155 in a downwardly projecting sleeve 156. A spring 162 provides spring pressure to bias the lifter upwardly.

From the foregoing it will be seen that the surgeon merely places the device onto the vessel to be opened, and he forces the hook 24 or 124 into the vessel and lifts the vessel portion 17 upwardly to an extent desired, as shown by the indicator 38 and 138 pointing to the indicia 26 or 126. The indicia 126 are carried on the leg 145, as shown in FIGS. 8 and 9. By pressing together the box-shaped cutting edges 30 on the inwardly facing side of the cutters 28 or 128, the device may be made to sever the lifted portion 17 therebetween leaving the severed vessel wall within the cutters and above the hole 11 now formed through the vessel wall 14 extending from an outer edge or aperture 21 of the hole 11 to the inner edge or aperture 19 at the interior surface 18 of the vessel 15.

From the foregoing it will be seen that the present invention provides a new and inexpensive surgical instrument which can be used to make more consistent and more uniform openings or holes in a vessel than heretofore. The lifter hooks the inner surface of the vessel wall and lifts the lifted portion a calibrated distance shown by the gauge means so that the surgeon can know with more certainty that the size of the hole 11 will be matched more closer to the donor vessel's interior surface or intima to which the vessel end will be attached.

While a preferred embodiment has been shown and described, it will be understood that there is no intent to limit the invention by such disclosure but, rather, it is intended to cover all modifications and alternate constructions falling within the spirit and scope of the invention as defined in the appended claims.

What is claimed is:
1. A surgical instrument for severing living tissue, said device comprising:
   a body,
   a lifter mounted on the body for vertical movement relative to the body, a hook means on the lifter for hooking the tissue and for lifting the tissue relative to the body through a predetermined distance, movable cutter means on the body movable from a non-cutting position to a cutting position to cut the tissue lifted by the hook means to form a cut of a predetermined size because of the lifting of the tissue through a predetermined distance, said hook means being centered on said body and lifting the tissue relative to the cutter means, said cutter means comprising a pair of pivotally mounted legs on said body each carrying a cutting blade for swinging toward one another to sever the tissue therebetween.

2. A surgical instrument in accordance with claim 1 in which said cutter blades have a substantially U-shaped cutting edge.

3. A surgical instrument in accordance with claim 2 in which said cutter blades are mounted on the lower free ends of the legs, upper ends of the legs being joined together.

4. A surgical instrument in accordance with claim 1 in which alignment means are provided for engagement with the pivotally mounted legs to keep the legs and the cutting blades aligned as the legs pivot the cutting blades to cut the tissue.

5. A surgical instrument in accordance with claim 3 including biasing means for biasing the legs apart, the surgeon pivoting the legs against the urging of the biasing means to sever the tissue.

6. A surgical instrument in accordance with claim 1 in which the cutters each comprise a box-shape body having an open side facing each other, a cutting edge around the edge of the open side of each box-shaped body, the tissue on the hook being disposed within the box-shaped bodies when the facing cutting edges on the respective cutters are brought together.

7. An arteriotomical device for severing an opening in a vessel wall having an interior lumen and an interior surface on the vessel wall, said device comprising:

a body having a pair of pivotally mounted legs movable from an open position to a closed severing position, a lifter mounted on the body for vertical movement relative to the legs, cutters on lower ends of each leg movable from the open position to the severing position to a portion of the vessel therebetween, and a hook on the lifter for insertion through the vessel wall and hooking the interior surface of the vessel wall for lifting a hooked portion of the vessel interior surface relative to the cutters through a predetermined distance, pivoting of the cutters from the open position toward the severing position causing the lowermost edges on the cutters to pass through the vessel wall along a path to sever an aperture of a predetermined size in the vessel's interior surface and to sever a hole through the vessel wall.

8. An arteriotomical device in accordance with claim 7 including gauge means on the device for indicating the amount of vertical movement of the vessel interior hooked surface relative to the lowermost edges on the cutters.

9. An arteriotomical device in accordance with claim 7 in which said cutters are box shaped with open sides facing each other and defined by U-shaped cutting edges.

10. An arteriotomical device in accordance with claim 7 in which alignment means are provided for engagement with the pivotally mounted legs to keep the legs and the cutters aligned during movement from the opened position to the severing position.

11. An arteriotomical device in accordance with claim 7 in which threaded portions are provided on said lifter and said body so that relative rotation of the respective threaded portions raises or lowers the hook relative to the cutters.

12. An arteriotomical device in accordance with claim 7 in which the cutters each comprise a box-shape body having an open side facing each other, a cutting edge around the edge of the open side of each box-shaped body, the tissue on the hook being disposed within the box-shaped bodies when the facing cutting edges on the respective cutters are brought together.

13. An arteriotomical device in accordance with claim 7 in which said lifter is a wire member and in which a stationary tube encircles the wire member for guiding the wire member for vertical sliding within the tube and for protecting the wire against bending.

* * * * *